US010420556B2

(12) United States Patent
Kostrzewski

(10) Patent No.: US 10,420,556 B2
(45) Date of Patent: Sep. 24, 2019

(54) SURGICAL STAPLING APPARATUS INCLUDING BUTTRESS ATTACHMENT

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/371,314

(22) Filed: Dec. 7, 2016

(65) Prior Publication Data
US 2017/0079653 A1 Mar. 23, 2017

Related U.S. Application Data

(63) Continuation of application No. 13/673,135, filed on Nov. 9, 2012, now abandoned.

(51) Int. Cl.
*A61B 17/068* (2006.01)
*A61B 17/072* (2006.01)
*A61B 17/32* (2006.01)

(52) U.S. Cl.
CPC ...... *A61B 17/07292* (2013.01); *A61B 17/068* (2013.01); *A61B 17/32* (2013.01); *A61B 2017/07257* (2013.01); *A61B 2017/07271* (2013.01); *A61B 2017/07285* (2013.01)

(58) Field of Classification Search
CPC . A61B 17/068; A61B 17/07292; A61B 17/32; A61B 2017/07257; A61B 2017/07271; A61B 2017/07285
USPC .......... 227/175.1–182.1; 606/219, 151, 153, 606/148, 232, 76, 77, 220, 149, 150, 139;
(Continued)

(56) References Cited

U.S. PATENT DOCUMENTS

| 3,054,406 A | 9/1962 | Usher |
| 3,079,606 A | 3/1963 | Bobrov et al. |
| 3,124,136 A | 3/1964 | Usher |

(Continued)

FOREIGN PATENT DOCUMENTS

| CA | 2282761 A1 | 9/1998 |
| DE | 1602563 U | 3/1950 |

(Continued)

OTHER PUBLICATIONS

European Office Action corresponding to counterpart Int'l Appln. No. EP 14 17 2681.0 dated May 13, 2016.
(Continued)

*Primary Examiner* — Alexander M Valvis
*Assistant Examiner* — Mary C Hibbert-Copeland

(57) ABSTRACT

A surgical stapling apparatus, a surgical stapling loading unit and a staple cartridge assembly are provided including a buttress releasably disposed against a tissue contacting surface of a cartridge assembly and/or an anvil assembly, a continuous length of suture securing a respective surgical buttress against the respective the tissue contacting surface, wherein the suture extends transversely across the respective surgical buttress, and a retaining feature securing each suture to the respective cartridge assembly and anvil assembly. The retaining feature may include an adhesive adhering the suture to a surface of the cartridge assembly and/or anvil assembly. The adhesive may adheres the suture to multiple locations along the surface of the cartridge assembly and/or anvil assembly.

19 Claims, 6 Drawing Sheets

(58) Field of Classification Search
USPC .............. 424/422, 551; 156/291; 602/41–79; 600/36–37
See application file for complete search history.

(56) References Cited

U.S. PATENT DOCUMENTS

| | | |
|---|---|---|
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A * | 5/1999 | Frater .............. A61B 17/07207 606/148 |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |

(56) References Cited

U.S. PATENT DOCUMENTS

| | | |
|---|---|---|
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |

(56) References Cited

U.S. PATENT DOCUMENTS

| | | |
|---|---|---|
| 8,920,443 B2 | 12/2014 | Hiles et al. |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,486,215 B2 | 11/2016 | Olson et al. |
| 9,504,470 B2 | 11/2016 | Milliman |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,931,116 B2 | 4/2018 | Racenet et al. |
| 10,022,125 B2 | 7/2018 | (Prommersberger) Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0028243 A1 | 3/2002 | Masters |
| 2002/0086990 A1 | 7/2002 | Kumar et al. |
| 2002/0091397 A1 | 7/2002 | Chen |
| 2002/0151911 A1 | 10/2002 | Gabbay |
| 2002/0165559 A1 | 11/2002 | Grant et al. |
| 2002/0165563 A1 | 11/2002 | Grant et al. |
| 2003/0065345 A1 | 4/2003 | Weadock |
| 2003/0078209 A1 | 4/2003 | Schmidt |
| 2003/0083676 A1 | 5/2003 | Wallace |
| 2003/0120284 A1 | 6/2003 | Palacios et al. |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0093029 A1 | 5/2004 | Zubik et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0143756 A1 | 6/2005 | Jankowski |
| 2005/0149073 A1 | 7/2005 | Arani et al. |
| 2005/0154093 A1 | 7/2005 | Kwon et al. |
| 2005/0228446 A1 | 10/2005 | Mooradian et al. |
| 2005/0245965 A1 | 11/2005 | Orban, III et al. |
| 2006/0004407 A1 | 1/2006 | Hiles et al. |
| 2006/0008505 A1 | 1/2006 | Brandon |
| 2006/0025816 A1 | 2/2006 | Shelton |
| 2006/0085030 A1 | 4/2006 | Bettuchi et al. |
| 2006/0085034 A1 | 4/2006 | Bettuchi |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0114262 A1 | 5/2007 | Mastri et al. |
| 2007/0123839 A1 | 5/2007 | Rousseau et al. |
| 2007/0175961 A1 | 8/2007 | Shelton et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |

(56) References Cited

U.S. PATENT DOCUMENTS

| | | |
|---|---|---|
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1* | 5/2009 | Tarinelli ............ A61B 17/07207 227/180.1 |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016888 A1 | 1/2010 | Calabrese et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1* | 4/2011 | Shah ................ A61B 17/07207 606/219 |
| 2011/0089220 A1 | 4/2011 | Ingmanson et al. |
| 2011/0089375 A1 | 4/2011 | Chan et al. |
| 2011/0215132 A1 | 9/2011 | Aranyi et al. |
| 2011/0270235 A1* | 11/2011 | Olson ............... A61B 17/07207 606/1 |
| 2011/0278346 A1 | 11/2011 | Hull et al. |
| 2011/0278347 A1 | 11/2011 | Olson et al. |
| 2011/0282446 A1 | 11/2011 | Schulte et al. |
| 2011/0293690 A1 | 12/2011 | Griffin et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |
| 2012/0187179 A1 | 7/2012 | Gleiman |
| 2012/0197272 A1 | 8/2012 | Oray et al. |
| 2012/0241493 A1 | 9/2012 | Baxter, III et al. |
| 2012/0241499 A1 | 9/2012 | Baxter, III et al. |
| 2013/0037596 A1 | 2/2013 | Bear et al. |
| 2013/0105548 A1 | 5/2013 | Hodgkinson et al. |
| 2013/0146641 A1 | 6/2013 | Shelton, IV et al. |
| 2013/0153636 A1 | 6/2013 | Shelton, IV et al. |
| 2013/0153639 A1 | 6/2013 | Hodgkinson et al. |
| 2013/0153641 A1 | 6/2013 | Shelton, IV et al. |
| 2013/0161374 A1 | 6/2013 | Swayze et al. |
| 2013/0209659 A1 | 8/2013 | Racenet et al. |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0097224 A1 | 4/2014 | Prior |
| 2014/0131418 A1 | 5/2014 | Kostrzewski |
| 2014/0138423 A1 | 5/2014 | Whitfield et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0203061 A1 | 7/2014 | Hodgkinson |
| 2014/0217148 A1 | 8/2014 | Penna |
| 2014/0224686 A1 | 8/2014 | Aronhalt et al. |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Willman |
| 2017/0119390 A1 | 5/2017 | Schellin et al. |
| 2017/0150967 A1 | 6/2017 | Hodgkinson et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | (Prommersberger) Stopek et al. |
| 2019/0021734 A1 | 1/2019 | Hodgkinson |
| 2019/0059878 A1 | 2/2019 | (Tarinelli) Racenet et al. |
| 2019/0083087 A1 | 3/2019 | Viola et al. |

FOREIGN PATENT DOCUMENTS

| | | |
|---|---|---|
| DE | 19924311 A1 | 11/2000 |
| EP | 0 327 022 A2 | 8/1989 |
| EP | 0 594 148 A1 | 4/1994 |
| JP | 2000-166933 A | 6/2000 |
| JP | 2002-202213 A | 7/2002 |

(56) References Cited

FOREIGN PATENT DOCUMENTS

| | | |
|---|---|---|
| JP | 2007-124166 A | 5/2007 |
| WO | 90/05489 A1 | 5/1990 |
| WO | 95/16221 A1 | 6/1995 |
| WO | 98/38923 A1 | 9/1998 |
| WO | 99/26826 A2 | 6/1999 |
| WO | 00/10456 A1 | 3/2000 |
| WO | 00/16684 A1 | 3/2000 |
| WO | 2010/075298 A2 | 7/2010 |

OTHER PUBLICATIONS

Extended European Search Report corresponding to counterpart Int'l Appln. No. EP 16 15 3647.9 dated Jun. 3, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Chinese First Office Action corresponding to counterpart Int'l Appln. No. CN 2013107068710 dated Dec. 16, 2016.
Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013206777 dated Feb. 1, 2017.
Chinese Second Office Action corresponding to counterpart Int'l Appln. No. CN 2013103036903 dated Feb. 23, 2017.
Japanese Office Action corresponding to counterpart Int'l Appln. No. JP 2013-175379 dated Mar. 1, 2017.
Chinese First Office Action corresponding to counterpart Int'l Appln. No. CN 201410028462.4 dated Mar. 2, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Canadian Office Action corresponding to counterpart Int'l Appln. No. CA 2,665,206 dated Nov. 19, 2013.
Chinese Notification 2, 2015 of Reexamination corresponding to counterpart Int'l Appln. No. CN 201010517292.8 dated Jun. 2, 2015.
Japanese Office Action corresponding to counterpart Int'l Appln. No. JP 2014-216989 dated Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 dated Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.

(56) References Cited

OTHER PUBLICATIONS

Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013l; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 20, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).

(56) References Cited

OTHER PUBLICATIONS

Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.

\* cited by examiner

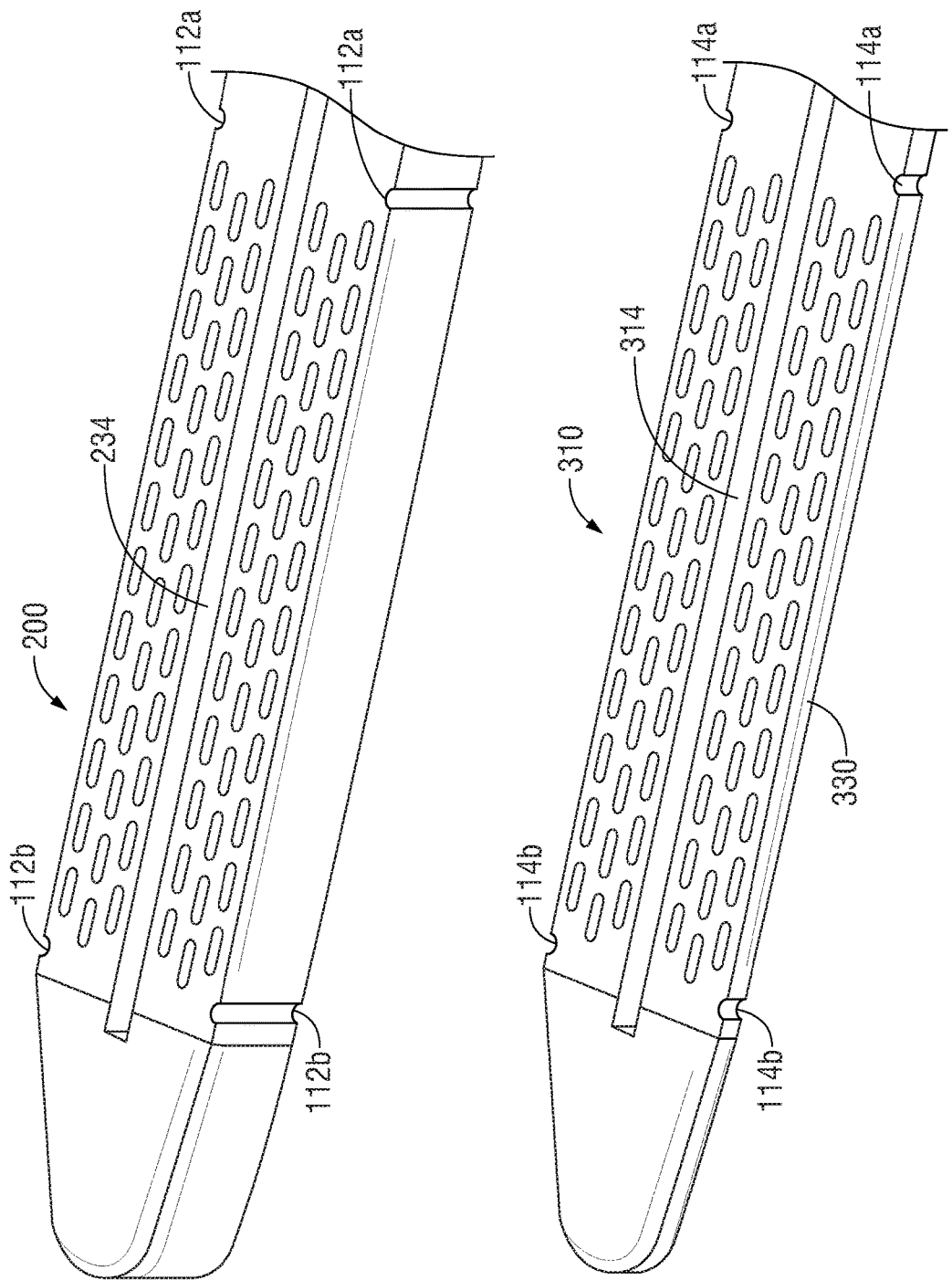

SURGICAL STAPLING APPARATUS INCLUDING BUTTRESS ATTACHMENT

CROSS-REFERENCE TO RELATED APPLICATIONS

This application is a Continuation Application which claims the benefit of and priority to U.S. patent application Ser. No. 13/673,135, filed on Nov. 9, 2012, the entire content of which is hereby incorporated by reference.

BACKGROUND

1. Technical Field

The present disclosure relates to a surgical stapling apparatus and, more particularly, to a surgical stapling apparatus including a detachable surgical buttress for an anvil assembly and/or a staple cartridge assembly.

2. Background of Related Art

Surgical stapling instruments that are used to sequentially or simultaneously apply one or more rows of fasteners to join segments of body tissues are well known in the art. The fasteners are typically in the form of surgical staples but two part polymeric fasteners can also be utilized. Such devices generally include a pair of jaws to clamp therebetween the body tissues to be joined. Typically, one of the jaw members includes or supports a staple cartridge assembly which accommodates a plurality of staples arranged in at least two lateral rows while the other jaw member has an anvil assembly that defines a surface for forming the staple legs as the staples are driven from the staple cartridge assembly.

When the stapling instrument is actuated, longitudinally translating cams contact staple drive members in one of the jaws which in turn acts upon staple pushers to sequentially or simultaneously eject the staples from the staple cartridge assembly. A blade can travel between the staple rows to longitudinally cut and/or open the stapled tissue between the rows of staples. Such instruments are disclosed, for example, in U.S. Pat. Nos. 3,079,606 and 3,490,675, the entire disclosures of which are hereby incorporated by reference herein.

When stapling relatively thin or fragile tissues, it may be important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible fabric reinforcing material, or a "buttress," between the staple and the underlying tissue. In this method, a layer of buttress material is placed against the tissue and the tissue is stapled in conventional manner. In more recent methods, the layer of buttress is positioned on the surgical stapling apparatus itself prior to stapling the tissue. Some surgical staplers utilize fasteners or clips to temporarily connect buttress material to each of the jaws of the staplers, i.e., one disposed on the staple cartridge assembly and the other on the anvil assembly.

It is a desire of the present application to provide a staple line reinforcement material that is securely attached to a jaw of a stapling instrument, while being releasable therefrom. It would also be desirable to provide a staple line reinforcement material or buttress that is releasably attached to a stapler jaw by a member that is removed from the site with the stapler after use. Accordingly, it is an object of this disclosure to meet the aforementioned desires.

SUMMARY

The present disclosure relates to a surgical stapling apparatus including a surgical buttress.

According to an aspect of the present disclosure, a surgical stapling apparatus is provided and includes a first jaw and a second jaw movable relative to one another to perform a surgical stapling operation whereby staples are fired into target tissue. The surgical stapling apparatus comprises a housing; a handle supported by the housing; an elongated body extending distally from the housing and having a distal end adapted to releasably engage a loading unit; and a loading unit supportable on a distal end of the housing.

According to another aspect of the present disclosure, a surgical stapling loading unit including a first jaw and a second jaw movable relative to one another to perform a surgical stapling operation whereby staples are fired into target tissue is provided.

The loading unit includes a cartridge assembly supportable on one of the first jaw and the second jaw, the cartridge assembly having a tissue contacting surface defining a longitudinally extending elongate slot and a plurality of staple retaining slots formed therein, wherein the cartridge assembly includes a surgical staple loaded into each staple retaining slot. The loading unit includes an anvil assembly supported on another of the first jaw and the second jaw, the anvil assembly including an anvil plate having a tissue contacting surface defining a longitudinally extending elongate slot and a plurality of staple forming pockets.

The loading unit includes a surgical buttress releasably disposed against at least one of the tissue contacting surface of the cartridge assembly and the tissue contacting surface of the anvil assembly, each surgical buttress including a body portion configured and dimensioned to overlie the plurality of staple retaining slots and the plurality of staple forming pockets of the respective cartridge assembly and anvil assembly, the body portion defining a distal edge and a proximal edge.

The loading unit includes a length of suture securing a respective surgical buttress against the at least one of the tissue contacting surface of the cartridge assembly and the tissue contacting surface of the anvil assembly, wherein the suture extends transversely across the respective surgical buttress.

The loading unit includes a retaining feature securing each suture to the respective cartridge assembly and anvil assembly.

Portions of the continuous suture may extend across both a distal portion and a proximal portion of each surgical buttress. Portions of the continuous suture may extend across a rear surface of the respective cartridge assembly and anvil assembly. Portions of the continuous suture may be threaded through the surgical buttress along opposed sides of the surgical buttress.

The retaining feature may include an adhesive adhering the suture to a surface of the respective cartridge assembly and anvil assembly. The adhesive may adhere the suture to multiple locations along the surface of the respective cartridge assembly and anvil assembly. The adhesive may adhere a portion of the suture to the surface of the cartridge assembly at a location near the distal edge of the surgical buttress. The adhesive may adhere a portion of the suture to the surface of the anvil assembly at a location near the proximal edge of the surgical buttress.

Each surgical buttress may include a tab extending from each side edge of the body portion, and an aperture formed in each tab, wherein the suture extends through each aperture.

Each of the cartridge assembly and the anvil assembly may include a plurality of grooves formed in a side surface of the respective cartridge assembly and anvil assembly, wherein each groove is configured and dimensioned to receive a length of suture therein, and wherein grooves are formed near opposed distal side edges and opposed proximal side edges of the respective cartridge assembly and anvil assembly.

According to a further aspect of the present disclosure, a surgical staple cartridge assembly configured for use with a surgical stapling apparatus, is provided. The staple cartridge assembly comprises a staple cartridge body defining a tissue contacting surface; a central longitudinally extending knife slot formed in the cartridge body; and a plurality of longitudinally extending rows of staple retaining pockets formed in the cartridge body.

The staple cartridge assembly further comprises a surgical staple loaded in each staple retaining slots; a plurality of pushers slidably supported for vertical translation in the cartridge body and operatively associated with the surgical staples; and an actuation sled slidably supported in longitudinal translation in the cartridge body and operatively associated with the plurality of pushers.

The staple cartridge assembly also comprises a surgical buttress releasably disposed against the tissue contacting surface of the cartridge body, the surgical buttress including a body portion configured and dimensioned to overlie the plurality of staple retaining slots of the cartridge body, the body portion of the surgical buttress defining a distal edge and a proximal edge.

The staple cartridge assembly additionally comprises a continuous length of suture securing the surgical buttress against the tissue contacting surface of the cartridge body, wherein the suture extends transversely across the surgical buttress, wherein portions of the continuous suture extend across both a distal portion and a proximal portion of each surgical buttress; and a retaining feature securing the suture to the cartridge body, wherein the retaining feature includes an adhesive adhering the suture to a surface of the cartridge body.

Portions of the continuous suture may extend across a rear surface of the cartridge body. Portions of the continuous suture may be threaded through the surgical buttress along opposed sides of the surgical buttress.

The adhesive may adhere the suture along the surface of the cartridge body. The adhesive may adhere a portion of the suture to the surface of the cartridge body at a location near the distal edge of the surgical buttress.

The surgical buttress may include a tab extending from each side edge of the body portion, and an aperture formed in each tab, wherein the suture extends through each aperture.

BRIEF DESCRIPTION OF THE DRAWINGS

The present disclosure will be further described with reference to the accompanying drawings, wherein like reference numerals refer to like parts in the several views, and wherein:

FIG. 10 is a schematic, perspective view of a distal end of the cartridge assembly and the anvil assembly, illustrating an alternate embodiment of a retaining feature of the present application.

DETAILED DESCRIPTION OF EMBODIMENTS

Figure 1:
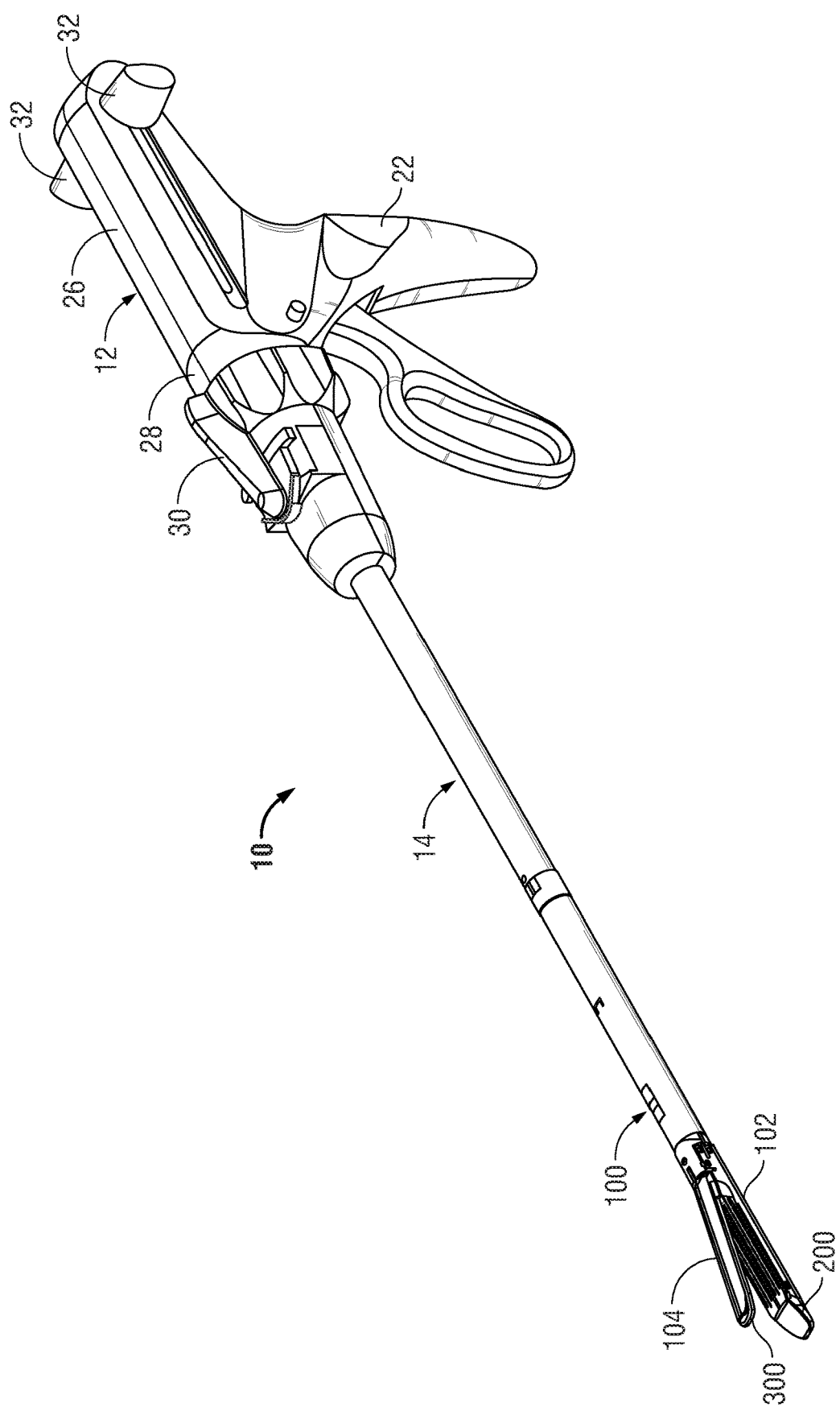
FIG. 1 is a perspective view of a surgical stapling apparatus according to an embodiment of the present disclosure.

Embodiments of the presently disclosed staple line reinforcement for a surgical stapling apparatus will now be described in detail with reference to the drawings, in which like reference numerals designate identical or corresponding elements in each of the several views. In the drawings and in the description that follows, the term "proximal," as is traditional, will refer to the end of the stapling apparatus which is closest to the operator, while the term "distal" will refer to the end of the apparatus which is farthest from the operator.

Referring now to FIG. 1, there is disclosed a linear surgical stapling apparatus, generally referred to as 10. In the interest of brevity, this disclosure will focus primarily on a buttress utilized in a loading unit 100, e.g., a single use loading unit ("SULU") or a disposable loading unit ("DLU"). For simplicity, hereinafter, SULU or DLU will be referred to as "DLU," but it should be understood to include either or both a DLU or SULU. An exemplary example of this type of surgical stapling instrument is disclosed in U.S. Pat. No. 8,011,555, the entire disclosure of which is incorporated by reference herein. The loading unit is removable and replaceable. Additionally or alternatively, the staple cartridge assembly can be removable and replaceable.

With reference to FIG. 1, surgical stapling apparatus 10 generally includes a handle assembly 12 and an elongate body 14 extending distally from handle assembly 12. A DLU 100 is releasably secured to the distal end of elongate body 14. DLU 100 includes a cartridge receiving jaw 102 configured to selectively receive a cartridge assembly 200 housing a plurality of surgical fasteners or staples 223 (see FIG. 4). DLU 100 further includes an anvil jaw 104, supporting an anvil assembly 300, movably secured in relation to cartridge receiving jaw 102. Handle assembly 12 includes a stationary handle member 22, a movable handle member 24, and a barrel portion 26. An articulation lever 30 is mounted on the forward end of barrel portion 26 adjacent rotatable member 28 to facilitate articulation of DLU 100. A pair of knobs 32 is movably positioned along barrel portion 26. Knobs 32 are advanced distally to approximate or close jaws 102, 104, and retracted proximally to unapproximate or open jaws 102, 104. Actuation of movable handle member 24 applies lines of staples 223 to tissue. In order to properly orient jaws 102, 104 relative to the tissue to be stapled, surgical stapling apparatus 10 is additionally provided with a rotatable member 28 on the forward end of barrel portion 26. Rotation of rotatable member 28 relative to handle assembly 12 rotates elongate body 14 and DLU 100 relative to handle assembly 12 so as to properly orient jaws 102, 104 relative to the tissue to be stapled.

Figure 2:
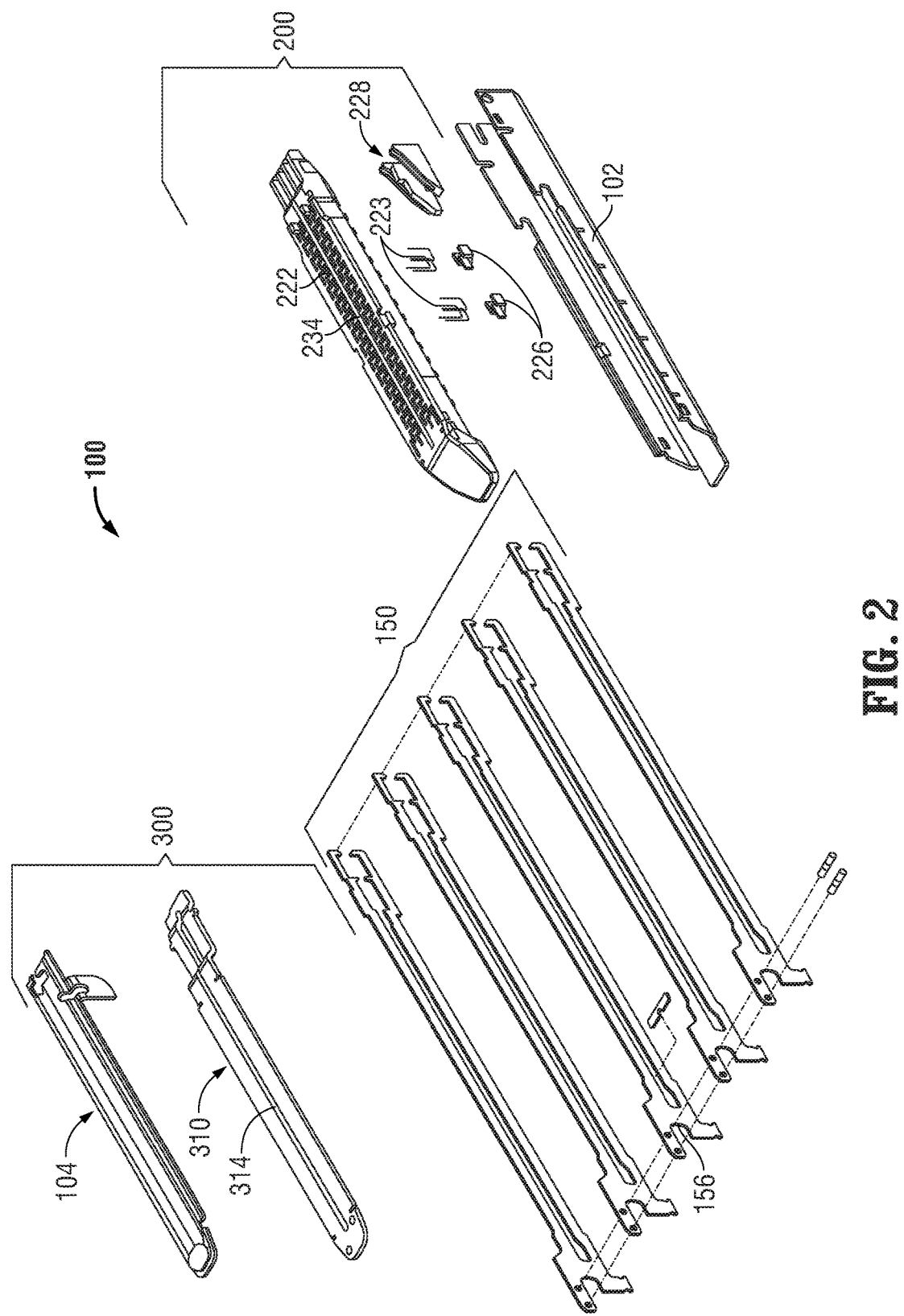
FIG. 2 is a perspective view, with parts separated, of an end effector of the surgical stapling apparatus of FIG. 1.
Figure 3:
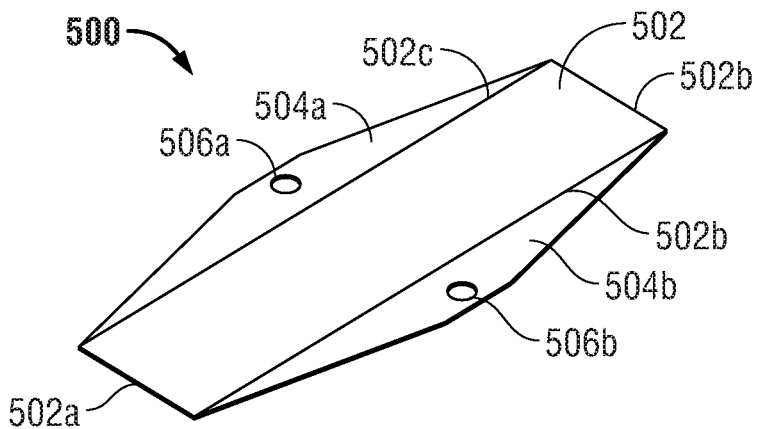
FIG. 3 is a top, perspective view of a surgical buttress of the present disclosure, shown in a planar condition.
Figure 4:
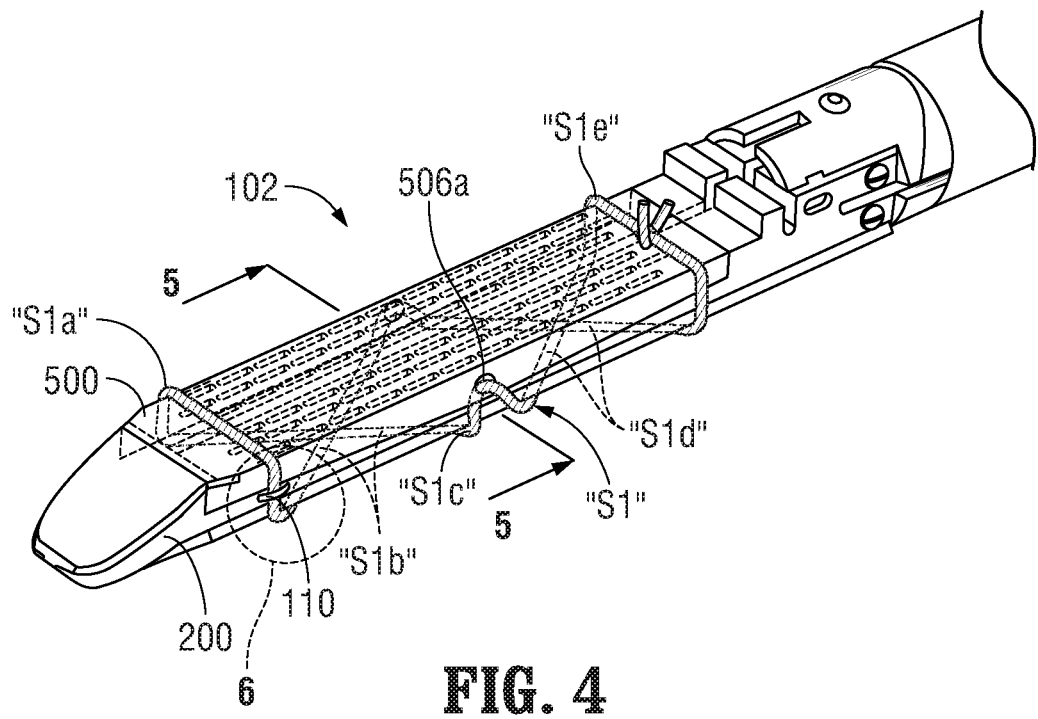
FIG. 4 is a top, perspective view of a distal end of a cartridge receiving jaw of the surgical stapling apparatus of FIG. 1, illustrating the surgical buttress of FIG. 3 secured thereto a staple cartridge assembly loaded therein.

As seen in FIGS. 2-4, cartridge receiving jaw 102 is dimensioned and configured to selectively receive a staple cartridge assembly 200 therein. Staple cartridge assembly 200 includes retention slots 222 formed therein for receiving a plurality of fasteners or staples 223 and pushers 226. A central longitudinal slot 234 is formed in and extends along the length of staple cartridge assembly 200 to facilitate passage therethrough of knife blade 156 of a drive bar 150 of surgical stapling apparatus 10. During operation of surgical stapling apparatus 10, an actuation sled 228 translates through staple cartridge assembly 200 to advance cam wedges of actuation sled 228 into sequential contact with pushers 226, to cause pushers 226 to translate vertically within retention slots 222 and urge staples 223 from slots 222 into staple forming pockets 312 of anvil plate 310 of anvil assembly 300 (see FIGS. 2 and 8). Reference may once again be made to U.S. Pat. No. 8,011,555, the entire disclosure of which is incorporated by reference herein, for a detailed discussion of the construction and operation of staple cartridge assembly 200.

As seen in FIGS. 4-9, at least one of cartridge receiving jaw 102 (including staple cartridge assembly 200), and anvil jaw 104 (including anvil assembly 300), includes a surgical buttress 500 operatively secured to a respective tissue contacting surface thereof.

As seen in FIG. 3, each surgical buttress 500 includes a rectangular central body portion 502 configured and dimensioned to overlie at least a portion of the staple retention slots 222 of the staple cartridge assembly 200, and staple forming pockets 312 of anvil plate 310 of anvil assembly 300. Body portion 502 defines a distal edge 502a, a proximal edge 502b, and a pair of side edges 502c, 502d.

Each surgical buttress 500 includes a first flap or tab 504a extending from a first side edge 502c of body portion 502, and a second flap or tab 504b extending from a second side edge 502d of body portion 502. Each flap 504a, 504b defines a respective aperture 506a, 506b formed therein, wherein apertures 506a, 506b are located at about a mid point of a length of body portion 502. Each flap 504a, 504b is substantially triangular in configuration. It is contemplated that buttress 500 may include a line of reduced thickness along side edges 502c, 502d to enable flaps 504a, 504b to be bent out of plane relative to a plane defined by body portion 502. The line of reduced thickness may also be used to facilitate removal of the flap or flaps from the main or body portion of the buttress.

The material from which the surgical buttress 500 is formed may be bioabsorbable or non-bioabsorbable. It should be understood that any combination of natural, synthetic, bioabsorbable and non-bioabsorbable materials may be used to form the buttress material. The buttress material may be porous or non-porous, combination of porous and non-porous layers. The non-porous buttress material may be utilized to retard or prevent tissue ingrowth from surrounding tissues thereby acting as an adhesion barrier and preventing the formation of unwanted scar tissue.

Additional exemplary materials for surgical buttresses 500 for use with the surgical stapling devices disclosed herein are set forth in commonly assigned U.S. Pat. Nos. 5,542,594; 5,908,427; 5,964,774; and 6,045,560, and commonly assigned U.S. Application Publication Nos. 2006/0085034, filed on Apr. 20, 2006; and 2006/0135992, filed on Jun. 22, 2006, the entire contents of each of which is incorporated herein by reference.

In an embodiment, surgical buttresses 500 may be fabricated from a suitable biocompatible and bioabsorbable material. Surgical buttresses 500 may also be fabricated from a non-absorbent material which does not retain fluid, for example, surgical buttresses 500 may be fabricated from "BIOSYN™" (a synthetic polyester, commercially available from Tyco Healthcare Group, LP d/b/a COVIDIEN, North Haven, Conn.), which is made from "GLYCOMER 631" (a block copolymer) which is a synthetic polyester composed of glycolide, dioxanone and trimethylene carbonate. The buttress can be a film, mesh, woven, non-woven, braided material or other material. It can be made by molding, drawing, weaving, using melt blown or spun bonding techniques or other techniques.

One block of the resulting copolymer contains randomly combined units derived from p-dioxanone (1,4-dioxan-2-one) and trimethylene carbonate (1,3-dioxan-2-one). A second block of the copolymer contains randomly combined units derived from glycolide and p-dioxanone. The resulting polyester is an ABA triblock terpolymer possessing about 60% glycolide, about 14% dioxanone, and about 26% trimethylene carbonate. Another co-polymer of glycolide trimethylene carbonate can be used to make the buttress.

Surgical buttresses 500 may be secured (i.e., from the manufacturer) onto anvil assembly 300 and/or cartridge-receiving-jaw 102/cartridge-assembly 200 combo either during the manufacturing process (i.e., pre-loaded) or prior to the surgical procedure while in the operating room. Additional or replacement surgical buttresses 500 for anvil assembly 300 and/or cartridge-receiving-jaw 102/cartridge-assembly 200 combo may be secured to either anvil assembly 300 or cartridge-receiving-jaw 102/cartridge-assembly 200 combo as needed or desired.

Figure 5:
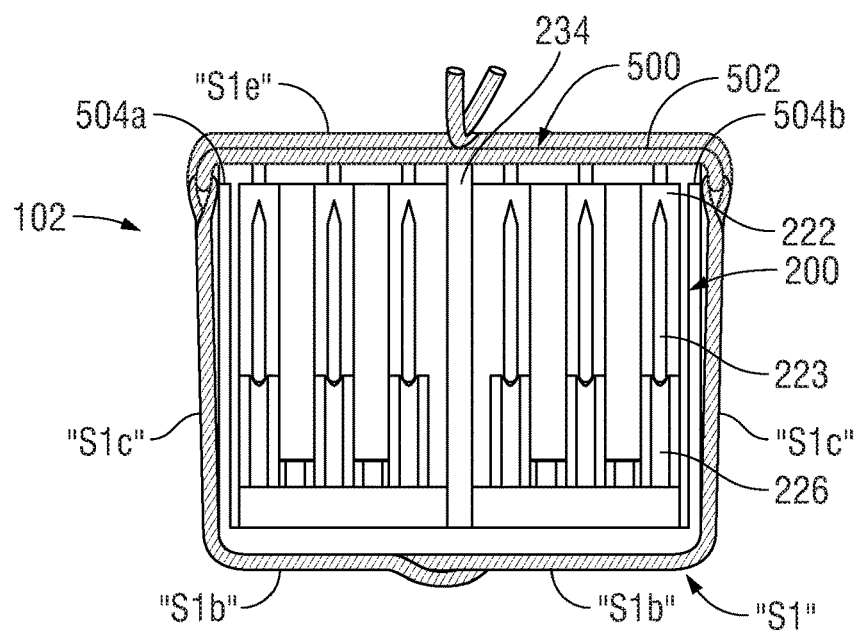
FIG. 5 is a cross-sectional view of the cartridge receiving jaw of FIG. 4, as taken through 5-5 of FIG. 4.
Figure 6:
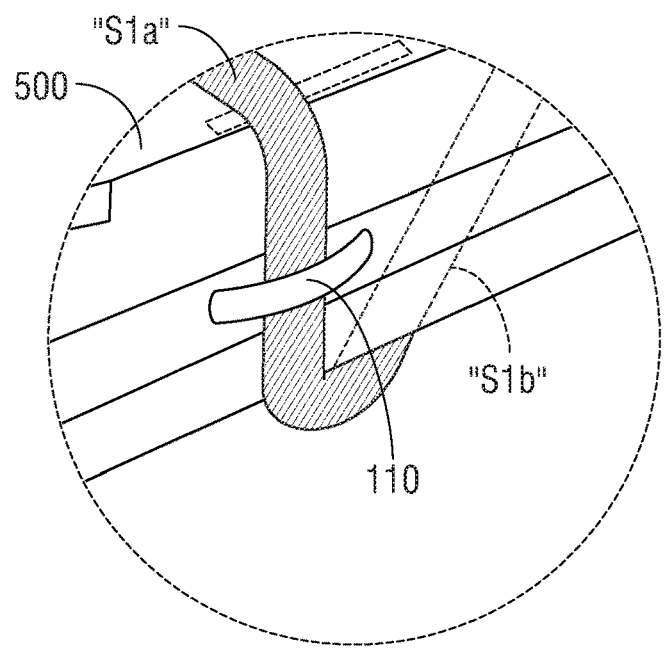
FIG. 6 is an enlarged view of the indicated area of detail of FIG. 4.

As seen in FIGS. 4-6, surgical buttress 500 is secured to cartridge receiving jaw 102 and to surgical cartridge assembly 200 by a length of a first suture "S1." The length of suture is desirably continuous so that only a single strand for each buttress is used. In any of the embodiments disclosed herein, more than one strand may be used to secure the buttress. With surgical buttress 500 placed against the tissue contacting surface of surgical cartridge assembly 200, such that body portion 502 of surgical buttress 500 overlies staple retention slots 222 of the staple cartridge assembly 200, first suture "S1" is used to strap, tie or otherwise secure surgical buttress 500 to the cartridge-receiving-jaw 102/cartridge-assembly 200 combo.

In particular, a first portion "S1a" of first suture "S1" is extended transversely across a distal end of staple cartridge assembly 200 (and a distal end of cartridge receiving jaw 102) in relative close proximity to distal edge 502a of surgical buttress 500. First suture "S1" is then extended to wrapped around each side of staple cartridge assembly 200 (and a distal end of cartridge receiving jaw 102) such that a pair of second portions "S1b" of first suture "S1" extend beneath staple cartridge assembly 200 (and distal end of cartridge receiving jaw 102). The pair of second portions "S1b" of first suture "S1" are crossed and then threaded through respective apertures 506a, 506b of flap 504a, 504b, such that a pair of third portions "S1c" of first suture "S1" engages respective flaps 504a, 504b. First suture "S1" is then once again extended to wrapped around each side of staple cartridge assembly 200 (and now a mid portion of cartridge receiving jaw 102) such that a pair of fourth portions "S1d" of first suture "S1" extend beneath staple cartridge assembly 200 (and mid portion of cartridge receiving jaw 102). The pair of fourth portions "S1d" of first suture "S1" are crossed and then extended to wrapped around each side of staple cartridge assembly 200 (and a proximal end of cartridge receiving jaw 102) such that the pair of fourth portions "S1d" of first suture "S1" extend above staple cartridge assembly 200 (and proximal end of cartridge receiving jaw 102). The remaining free ends "S1e" (i.e., a pair of fifth portions) of first suture "S1" are then tied or secured to one another, while extending transversely across the proximal end of staple cartridge assembly 200 (and the proximal end of cartridge receiving jaw 102) in relative close proximity to proximal edge 502b of surgical buttress 500.

In accordance with the present disclosure, a retaining feature is provided to secure first portion "S1a" of first suture "S1" in relatively close proximity to distal edge 502a of surgical buttress 500. In particular, the retaining feature may include a dab of adhesive 110 applied against staple cartridge assembly 200 (or a distal end of cartridge receiving jaw 102) at a location to adhere or secure first portion "S1a" of first suture "S1" in relatively close proximity to distal edge 502a of surgical buttress 500 prior to second portions "S1b" of first suture "S1" extending around each side and beneath staple cartridge assembly 200 (and a distal end of cartridge receiving jaw 102). Alternatively, in any of the embodiments disclosed herein, the suture may be attached to the jaw using welding, mechanical features, or other techniques. In alternate embodiments, a retaining feature may also be provided to secure fifth portion "S1e" of first suture "S1" in relatively close proximity to proximal edge 502b of surgical buttress 500.

Additionally, first portion "S1a" of first suture "S1" is adhered or secured to staple cartridge assembly 200 (or a distal end of cartridge receiving jaw 102) at a location such that first portion "S1a" of first suture "S1" extends transversely across central longitudinal slot 234 of staple cartridge assembly 200.

In accordance with the present disclosure, it is contemplated that the retaining features may include a tacking of first suture "S1" against staple cartridge assembly 200 (or a distal end of cartridge receiving jaw 102), at a location to maintain first portion "S1a" of first suture "S1" in relatively close proximity to distal edge 502a of surgical buttress 500, by a welding process or the like.

In a further embodiment, as seen in FIG. 10, it is contemplated that the cartridge assembly 200 may include a groove or notch 112a formed in each side surface of staple cartridge assembly 200 (and/or cartridge receiving jaw 102), at a location to maintain first portion "S1a" of first suture "S1" in relatively close proximity to distal edge 502a of surgical buttress 500, and which are configured to receive a segment of first suture "S1" therein. A groove or notch 112b may also be formed in each side surface of staple cartridge assembly 200 (and/or cartridge receiving jaw 102), at a location to maintain fifth portion "S1e" of first suture "S1" in relatively close proximity to proximal edge 502b of surgical buttress 500, and which are configured to receive a segment of first suture "S1" therein.

Reference may be made to U.S. patent application Ser. No. 13/404,134, filed on Feb. 24, 2012, and to U.S. Pat. No. 8,011,555, the entire content of each of which is incorporated herein by reference, for a detailed disclosure of the configuration of groove-type or notch-type retaining features.

In accordance with the present disclosure, it is contemplated that surgical buttress 500 may be secured or tied solely to staple cartridge assembly 200. As such, a staple cartridge assembly 200, including a surgical buttress 500 secured or tied thereto, may be loaded into the cartridge receiving jaw 102 of surgical stapling apparatus 10.

Figure 7:
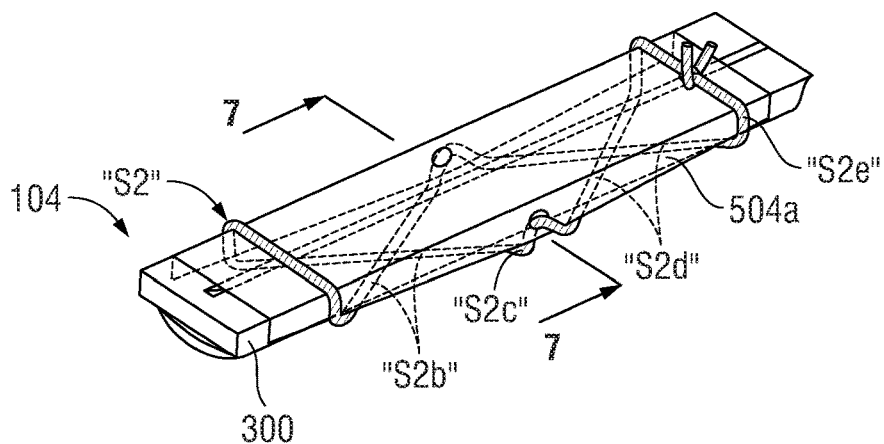
FIG. 7 is a bottom, perspective view of a distal end of an anvil jaw of the surgical stapling apparatus of FIG. 1, illustrating the surgical buttress of FIG. 3 secured thereto.
Figure 8:
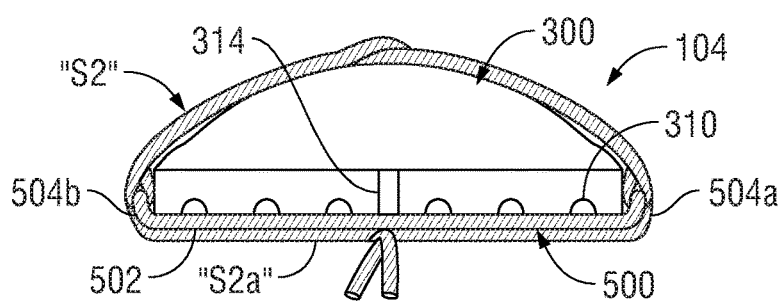
FIG. 8 is a cross-sectional view of the anvil jaw of FIG. 7, as taken through 8-8 of FIG. 7.
Figure 9:
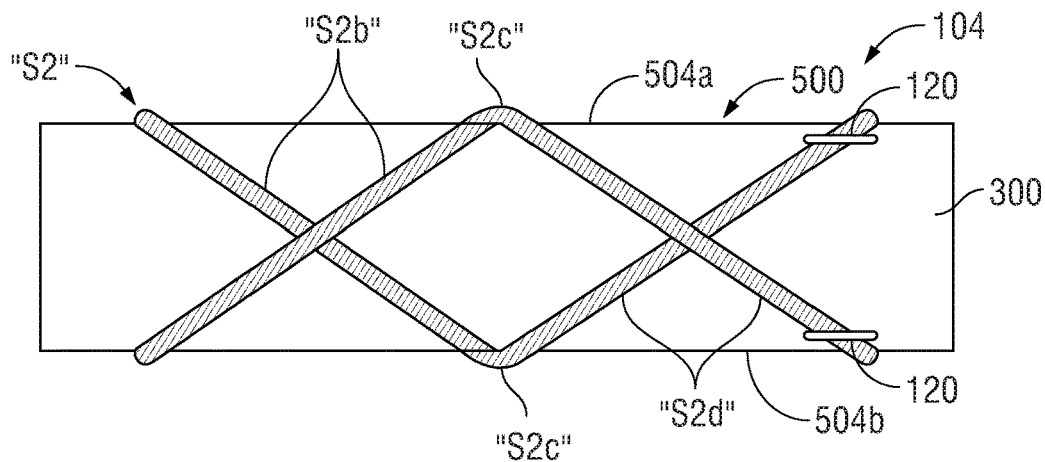
FIG. 9 is a top, plan view of the anvil jaw of FIG. 7.

As seen in FIGS. 7-9, surgical buttress 500 is secured to anvil jaw 104 by a continuous length of a second suture "S2." With surgical buttress 500 placed against the tissue contacting surface of anvil plate 310 of anvil assembly 300 (or anvil jaw 104), such that body portion 502 of surgical buttress 500 overlies staple forming pockets 312 of anvil plate 310, second suture "S2" is used to strap, tie or otherwise secure surgical buttress 500 to the anvil assembly 300 (and/or anvil jaw 104).

In particular, a first portion "S2a" of second suture "S2" is extended transversely across a distal end of anvil jaw 104 in relative close proximity to distal edge 502a of surgical buttress 500. Second suture "S2" is then extended to wrapped around each side of the anvil assembly 300 (and/or anvil jaw 104) such that a pair of second portions "S2b" of second suture "S2" extend beneath the anvil assembly 300 (and/or anvil jaw 104). The pair of second portions "S2b" of second suture "S2" are crossed and then threaded through respective apertures 506a, 506b of flap 504a, 504b, such that a pair of third portions "S2c" of second suture "S2" engages respective flaps 504a, 504b. Second suture "S2" is then once again extended to wrapped around each side of the anvil assembly 300 (and/or anvil jaw 104) such that a pair of fourth portions "S2d" of second suture "S2" extend beneath the anvil assembly 300 (and/or anvil jaw 104). The pair of fourth portions "S2d" of second suture "S2" are crossed and then extended to wrapped around each side of the anvil assembly 300 (and/or anvil jaw 104) such that the pair of fourth portions "S2d" of second suture "S2" extend above the anvil assembly 300 (and/or anvil jaw 104). The remaining free ends "S2e" (i.e., a pair of fifth portions) of second suture "S2" are then tied or secured to one another, while extending transversely across the proximal end of the anvil assembly 300 (and/or anvil jaw 104) in relative close proximity to proximal edge 502b of surgical buttress 500.

Also in accordance with the present disclosure, a retaining feature is provided to secure fifth portions "S2e" of second suture "S2" in relatively close proximity to proximal edge 502b of surgical buttress 500. In particular, the retaining feature may include a dab of adhesive 120 applied against the anvil assembly 300 (and/or anvil jaw 104) at a location to maintain fifth portions "S2e" of second suture "S2" in relatively close proximity to proximal edge 502b of surgical buttress 500 following the fifth portions "S2e" being tied or otherwise joined together above staple the anvil assembly 300 (and/or anvil jaw 104). Preferably, the dab of adhesive 120 is applied to a rear surface of the anvil assembly 300 (and/or anvil jaw 104). In alternate embodiments a retaining feature may also be provided to secure first portion "S2a" of second suture "S2" in relatively close proximity to distal edge 502a of surgical buttress 500.

Additionally, first portion "S2a" of second suture "S2" is adhered or secured to the anvil assembly 300 (and/or anvil jaw 104) at a location such that first portion "S2a" of second suture "S2" extends transversely across central a longitudinal knife receiving slot formed in the anvil plate 310 of anvil assembly 300.

In an embodiment, it is contemplated that the retaining features may include a tacking of second suture "S2" against the anvil assembly 300 (and/or anvil jaw 104) at a location to maintain fifth portion "S2e" of second suture "S2" in relatively close proximity to proximal edge 502a of surgical buttress 500, by a welding process or the like.

As seen in FIG. 10, it is contemplated that the anvil assembly 300 may include a groove or notch 114a formed in a side surface of the anvil assembly 300 (and/or anvil jaw 104), at a location to maintain first portion "S2a" of second suture "S2" in relatively close proximity to distal edge 502a of surgical buttress 500, which is configured to receive a segment of second suture "S2" therein. A groove or notch 114b may also be formed in each side surface of the anvil assembly 300 (and/or anvil jaw 104), at a location to maintain fifth portion "S2e" of second suture "S2" in relatively close proximity to proximal edge 502b of surgical buttress 500, and which are configured to receive a segment of second suture "S2" therein.

Reference may once again be made to U.S. patent application Ser. No. 13/404,134, filed on Feb. 24, 2012 (Now U.S. Pat. No. 8,820,606), and to U.S. Pat. No. 8,011,555, the entire content of each of which is incorporated herein by reference, for a detailed disclosure of the configuration of groove-type or notch-type retaining features.

Buttresses 500 are provided to reinforce and seal staple lines applied to tissue by surgical stapling apparatus 10. Cartridge assembly 200 and anvil assembly 300 are particularly configured to allow surgical buttresses 500 to be localized on inwardly facing surfaces of cartridge assembly 200 and anvil assembly 300 in order to facilitate passage of surgical stapling apparatus 10 into the body of a patient without risk of tearing or wrinkling of the respective buttresses as surgical stapling apparatus 10 is inserted into and manipulated within the body of a patient.

In operation, with DLU 100 coupled to a distal end of elongated body 14 of surgical stapling apparatus 10, and with buttresses 500 loaded onto each of anvil assembly 300 and cartridge assembly 200, surgical stapling apparatus 10 is used in accordance with methods known by those skilled in the art. Once anvil assembly 300 and cartridge assembly 200 are clamped onto tissue, surgical stapling apparatus 10 is fired. In firing surgical stapling apparatus 10, a knife blade 156

As the knife blade 156 begins to travel distally, the knife blade 156 substantially simultaneously cuts through a central section of the fifth portions "S1e, S2e" of respective first and second sutures "S1, S2" of anvil assembly 300 and cartridge assembly 200, thereby respectively freeing the proximal ends of cartridge buttress 500a from cartridge assembly 200. Thereby loosening suture "S1" around cartridge buttress 500a. As the knife blade 156 is moved distally, the knife blade slices or cuts longitudinally through both buttresses 500, thereby dividing the buttresses 500 substantially in half.

Additionally, as the knife blade 156 approaches the distal-most position, the knife blade 156 cuts through first portion "S1a" of first suture "S1" which extends transversely across central longitudinal slot 234 of staple cartridge assembly 200 and through first portion "S2a" of second suture "S2" which extends transversely across central a longitudinal knife receiving slot 314 (see FIGS. 2 and 8) formed in the anvil plate 310 of anvil assembly 300, thereby respectively freeing the distal ends of anvil buttress 500b from anvil assembly 300. Thereby loosening sutures "S2" around anvil buttress 500b.

Since sutures "S1, S2" are adhered or otherwise secured to respective underlying components (i.e., cartridge jaw 102 and/or cartridge assembly 200, and assembly jaw 104 and/or anvil assembly 300), sutures "S1, S2" remain adhered or otherwise secured thereto following a firing of surgical stapling apparatus 10 and during a removal or withdrawal of DLU 100 from the operative site, thereby also withdrawing sutures "S1, S2" from the operative site.

In any of the embodiments disclosed herein, the sutures may comprise straps, cables, lines, tabs, belts or the like and are made from non-absorbable or bioabsorbable materials.

In any of the embodiments disclosed herein, the suture extends across the knife slot and is cut by the knife at least once. Desirably, the suture is attached to the stapler components such as the anvil assembly, cartridge assembly or channel, or both, so that each piece of the one or more pieces of suture per buttress is removed with the stapler instrument after it is fired.

While the above-described embodiments surgical staplers incorporating the use of movable knife blades to sever and release surgical buttresses from the tissue contacting surfaces of the anvil assembly and the cartridge assembly have been shown and described in relation to endoscopic surgical staplers, it is envisioned and within the scope of the present disclosure that any of the above-embodiments may be incorporated into any type of surgical stapler, including and not limited to open surgical staplers, such as, for example, linear surgical staplers and transverse surgical staplers.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A surgical stapling loading unit including a first jaw and a second jaw movable relative to one another to perform a surgical stapling operation, the loading unit comprising:
    a cartridge assembly supportable on the first jaw, the cartridge assembly having a tissue contacting surface defining an elongate slot having a knife blade disposed therein;
    an anvil assembly supported on the second jaw, the anvil assembly including an anvil plate having a tissue contacting surface defining an elongate slot configured to receive the knife blade;
    a surgical buttress including a continuous body portion defined by a proximal edge, a distal edge, a first side edge, and a second side edge, the surgical buttress having a first flap extending from the first side edge of the body portion and a second flap extending from the second side edge of the body portion;
    a length of suture securing the body portion of the surgical buttress against the tissue contacting surface of the cartridge assembly or the anvil assembly and the first and second flaps against side surfaces of the cartridge assembly or the anvil assembly, the length of suture extending transversely across a proximal portion of the surgical buttress, through the first flap, transversely across a distal portion of the surgical buttress, and through the second flap such that the length of suture is disposed in a looped configuration with end portions of the length of suture secured to one another and overlying the proximal portion of the surgical buttress, the proximal and distal portions overlying the elongate slot of the cartridge assembly or the anvil assembly, and the knife blade movable through the elongate slot from a proximal position to a distal position such that the knife blade cuts the length of suture at both the distal and proximal portions of the surgical buttress thereby releasing the surgical buttress from the tissue contacting surface; and a retaining feature securing the length of suture to the cartridge assembly or the anvil assembly such that the length of suture remains secured to the cartridge assembly or the anvil assembly when the surgical buttress is released therefrom.

2. The surgical stapling loading unit according to claim 1, wherein the length of suture extends across a rear portion of the cartridge assembly or the anvil assembly.

3. The surgical stapling loading unit according to claim 1, wherein the retaining feature is an adhesive adhering the length of suture to the side surfaces of the cartridge assembly or the anvil assembly.

4. The surgical stapling loading unit according to claim 3, wherein the adhesive adheres the length of suture to multiple locations along the side surfaces of the cartridge assembly or the anvil assembly.

5. The surgical stapling loading unit according to claim 1, wherein the retaining feature is an adhesive adhering the length of suture to a rear portion of the cartridge assembly or the anvil assembly.

6. The surgical stapling loading unit according to claim 1, wherein the first and second flaps extend substantially along an entire length of the first and second side edges of the body portion.

7. The surgical stapling loading unit according to claim 6, wherein each of the first and second flaps has a substantially triangular configuration.

8. The surgical stapling loading unit according to claim 1, wherein each of the first and second flaps has an aperture located about a midpoint of a length of the body portion, and the length of suture is threaded through the apertures.

9. The surgical stapling loading unit according to claim 8, wherein the length of suture includes:
a first portion extending transversely across the distal portion of the surgical buttress;
a pair of second portions extending around the side surfaces of the cartridge assembly or the anvil assembly and crossing one another about a rear portion of the cartridge assembly or the anvil assembly;
a pair of third portions threaded through respective apertures of the first and second flaps;
a pair of fourth portions extending around the side surfaces of the cartridge assembly or the anvil assembly, crossing one another about the rear portion of the cartridge assembly or the anvil assembly, and extending around the side surfaces of the cartridge assembly or the anvil assembly; and
the end portions extending transversely across the proximal portion of the surgical buttress.

10. The surgical stapling loading unit according to claim 9, wherein the retaining feature secures the pair of second portions of the length of suture to the side surfaces of the cartridge assembly or the anvil assembly.

11. The surgical stapling loading unit according to claim 1, wherein the cartridge assembly or the anvil assembly includes a plurality of grooves formed in the side surfaces thereof, wherein each groove of the plurality of grooves is configured and dimensioned to receive the length of suture therein, and wherein the plurality of grooves are formed near opposed distal side edges and opposed proximal side edges of the cartridge assembly or the anvil assembly.

12. A surgical staple cartridge assembly configured for use with a surgical stapling apparatus, the staple cartridge assembly comprising:
a staple cartridge body including a tissue contacting surface defining a central longitudinally extending knife slot having a knife blade disposed therein;
a surgical buttress including a continuous body portion defined by a proximal edge, a distal edge, a first side edge, and a second side edge, the surgical buttress having a first flap extending from the first side edge of the body portion and a second flap extending from the second side edge of the body portion;
a length of suture securing the body portion of the surgical buttress against the tissue contacting surface of the staple cartridge body and the first and second flaps against side surfaces of the staple cartridge body, the length of suture extending transversely across a proximal portion of the surgical buttress, through the first flap, transversely across a distal portion of the surgical buttress, and through the second flap such that the length of suture is disposed in a looped configuration with end portions of the length of suture secured to one another and overlying the proximal portion of the surgical buttress, the proximal and distal portions overlying the knife slot of the staple cartridge body, and the knife blade movable through the knife slot from a proximal position to a distal position such that the knife blade cuts the length of suture at both the distal and proximal portions of the surgical buttress thereby releasing the surgical buttress from the tissue contacting surface; and
a retaining feature securing the length of suture to the staple cartridge body such that the length of suture remains secured to the staple cartridge body when the surgical buttress is released therefrom.

13. The surgical staple cartridge assembly according to claim 12, wherein the retaining feature is an adhesive adhering the length of suture to the side surfaces of the staple cartridge body.

14. The surgical staple cartridge assembly according to claim 12, wherein the first and second flaps extending substantially along an entire length of the first and second side edges.

15. The surgical staple cartridge assembly according to claim 14, wherein each of the first and second flaps has a substantially triangular configuration.

16. The surgical staple cartridge assembly according to claim 14, wherein each of the first and second flaps has an aperture located about a midpoint of a length of the body portion, and the length of suture is threaded through the apertures.

17. The surgical staple cartridge assembly according to claim 16, wherein the length of suture includes:
a first portion extending transversely across the distal portion of the surgical buttress;
a pair of second portions extending around the side surfaces of the staple cartridge body and crossing one another about a rear portion of the staple cartridge body;
a pair of third portions threaded through respective apertures of the first and second flaps;
a pair of fourth portions extending around the side surfaces of the staple cartridge body, crossing one another about the rear portion of the staple cartridge body, and extending around the side surfaces of the staple cartridge body; and the end portions extending transversely across the proximal portion of the surgical buttress.

18. The surgical staple cartridge assembly according to claim 17, wherein the retaining feature secures the pair of second portions of the length of suture to the side surfaces of the staple cartridge body.

19. The surgical staple cartridge assembly according to claim 12, wherein the staple cartridge body includes a plurality of grooves formed in the side surfaces thereof, wherein each groove of the plurality of grooves is configured and dimensioned to receive the length of suture therein, and wherein the plurality of grooves are formed near opposed distal side edges and opposed proximal side edges of the staple cartridge body.

* * * * *